US00PP22281P3

(12) United States Plant Patent
Klemm et al.

(10) Patent No.: US PP22,281 P3
(45) Date of Patent: Nov. 29, 2011

(54) CARNATION PLANT NAMED 'KLEDP09102'

(50) Latin Name: *Dianthus caryophyllus*
Varietal Denomination: KLEDP09102

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,222

(22) Filed: Mar. 31, 2010

(65) Prior Publication Data

US 2011/0247115 P1 Oct. 6, 2011

(51) Int. Cl.
*A01H 5/00* (2006.01)

(52) U.S. Cl. ..... Plt./276

(58) Field of Classification Search ..... Plt./273, Plt./276

See application file for complete search history.

*Primary Examiner* — Susan McCormick Ewoldt

(74) *Attorney, Agent, or Firm* — Jondle & Associates, P.C.

(57) ABSTRACT

A new variety of carnation named 'KLEDP09102' particularly characterized by its nearly white flowers having a purple-pink center, a medium growth habit, and upright flower stems, is disclosed.

1 Drawing Sheet

Genus and species: *Dianthus caryophyllus*.
Variety denomination: 'KLEDP09102'.

BACKGROUND OF THE NEW PLANT

The present invention comprises a new and distinct variety of carnation botanically known as *Dianthus caryophyllus,* and hereinafter referred to by the variety name 'KLEDP09102'. 'KLEDP09102' was discovered as a seedling resulting from a cross conducted in June 2004 in Stuttgart, Germany between the proprietary female carnation plant, 'DCP 03 010' (unpatented) and the proprietary male carnation plant, 'DCP 03 212' (unpatented). A single plant selection was subsequently chosen for further evaluation and for asexual propagation.

The new variety was first propagated via vegetative cuttings in July 2005 in Stuttgart, Germany and has been asexually reproduced repeatedly by vegetative cuttings in Stuttgart, Germany for approximately seven to eight generations. 'KLEDP09102' has been found to retain its distinctive characteristics through successive asexual propagations via vegetative cuttings.

Plant Breeder's Rights for this variety have not been applied for. 'KLEDP09102' has not been made publicly available or sold more than one year prior to the filing date of this application.

SUMMARY OF THE INVENTION

The following are the most outstanding and distinguishing characteristics of this new variety when grown under normal commercial practices in a greenhouse in Stuttgart, Germany.

1. Nearly white flowers having a purple-pink center;
2. A medium growth habit; and
3. Upright flower stems.

DESCRIPTION OF THE PHOTOGRAPH

This new carnation plant is illustrated by the accompanying photograph which shows a close-up of a mature flower, flower buds, and foliage. The colors shown are as true as can be reasonably obtained by conventional photographic procedures. The photograph was taken in April 2009 of a 5-month-old plant grown from rooted cuttings in a 10 centimeter pot in a greenhouse (glasshouse) in Stuttgart, Germany under conditions which approximate those generally used in commercial practice.

DESCRIPTION OF THE NEW VARIETY

The following detailed descriptions set forth the distinctive characteristics of 'KLEDP09102'. The data which define these characteristics were collected from asexual reproductions carried out in Stuttgart, Germany. The plant history was taken in Spring 2009 on 5-month-old plants in 10 centimeter pots that were pinched once at week 45 and grown in a greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Caryophyllaceae.
- *Genus and species.*—*Dianthus caryophyllus.*
- *Common name.*—Carnation.

Parentage:
- *Female parent.*—The proprietary carnation 'DCP 03 010' (unpatented).
- *Male parent.*—The proprietary carnation 'DCP 03 212' (unpatented).

Plant:
- *Form.*—Potted plant.
- *Habit.*—Upright.
- *Height* (*from top of soil*).—10.0 cm to 15.0 cm.
- *Width* (*spread*).—15.0 cm to 20.0 cm.
- *Life cycle.*—Perennial partially.
- *Flowering habit.*—Continuous.

*Time to produce a finished flowering plant.*—5 months.
*Propagation type.*—Vegetative cuttings.
*Time to initiate roots.*—16 to 20 days.
*Root description.*—White, fine.
*Temperature tolerances.*—Normal.

Branches:
*Strength.*—Medium.
*Quantity per plant.*—6 to 8.
*Color.*—RHS N137A.
*Length.*—5.0 cm to 8.0 cm.
*Diameter.*—2.0 cm to 3.0 cm.
*Internode length.*—0.5 cm to 3.0 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Immature leaf (both upper and lower surfaces): RHS N138A. Mature leaf (both upper and lower surfaces): RHS 138A.
*Size.*—Length: 3.0 cm to 5.0 cm. Width: 0.4 cm to 0.7 cm.
*Texture.*—Smooth.
*Venation pattern.*—Pinnate.
*Venation color.*—Upper surface: RHS N138B. Lower surface: RHS N137B.
*Petioles.*—Absent.

Flowers:
*Type.*—Small sprays.
*Flowering season.*—Spring to Fall.
*Size.*—Width: 4.0 cm to 4.5 cm. Depth: 1.5 cm to 2.0 cm.
*Shape.*—Semi-concave.
*Fragrance.*—Strong.
*Number of flowers per plant.*—4 to 7.
*Calyx.*—Form: Cylinder vase. Length: 0.2 cm. Width: 1.2 cm.

Flower buds:
*Color.*—RHS 138B.
*Shape.*—Elliptic.
*Length.*—1.0 cm to 1.8 cm.
*Diameter.*—0.6 cm to 0.8 cm.

Petals:
*Arrangement.*—Arranged in several whorls.
*Quantity* (*per flower*).—Greater than 20.
*Shape.*—Spoon-shaped.
*Apex.*—Obtuse.
*Base.*—Acute.
*Margin.*—Serrated.
*Size.*—Length: 3.5 cm. Width: 1.7 cm.
*Color.*—When opening: Upper surface: RHS N66A to RHS N66B and RHS N69A at the edge. Lower surface: RHS N69B to RHS N69C. When fully opened: Upper surface: RHS N66B to RHS N66C and RHS 69D at the edge. Lower surface: RHS N69B to RHS N69C.
*Texture* (*both upper and lower surfaces*).—Smooth.

Sepals:
*Arrangement.*—Fused.
*Quantity* (*per flower*).—5.
*Shape.*—Elliptic.
*Apex.*—Acute.
*Base.*—Obtuse.
*Margin.*—Smooth.
*Size.*—Length: 1.0 cm to 1.8 cm. Width: 0.6 cm to 0.8 cm.
*Color.*—Upper surface: RHS 138B. Lower surface: RHS 138C.
*Texture* (*both upper and lower surfaces*).—Smooth.

Peduncle:
*Length.*—5.0 cm to 15.0 cm.
*Diameter.*—0.3 cm.
*Texture.*—Smooth.
*Color:*—RHS N138A.

Reproductive organs:
*Pistils.*—Quantity: 1. Style: Length: 0.5 cm to 1.0 cm. Color: RHS N155D. Stigma color: RHS N155D. Ovary color: RHS 144C.
*Stamens.*—Quantity: Moderate. Filament: Length: 0.3 cm to 0.8 cm. Color: RHS N155D. Anther color: RHS 62C. Pollen: Amount: Moderate. Color: Light pink.

Fruit and seed set: None observed.

Disease and insect resistance: No common diseases and insect resistance observed.

COMPARISON WITH PARENTAL AND COMMERCIAL VARIETIES

'KLEDP09102' differs from the female parent, the proprietary carnation 'DCP 03 010' (unpatented), in that 'KLEDP09102' has a medium growth habit and nearly white flowers with a purple-pink center, while 'DCP 03 010' has a strong growth habit and purple flowers.

'KLEDP09102' differs from the male parent, the proprietary carnation 'DCP 03 212' (unpatented), in that 'KLEDP09102' has a medium growth habit and white flowers with a purple-pink center, while 'DCP 03 212' has a compact growth habit and light pink flowers.

'KLEDP09102' differs from the commercial comparison variety 'KLEDP07088' (unpatented), in that 'KLEDP09102' has white flowers with a purple-pink center and upright flower stems, while 'KLEDP07088' has white flowers with a dark purple center and oblique flower stems.

We claim:

1. A new and distinct variety of carnation plant named 'KLEDP09102' as shown and described herein.

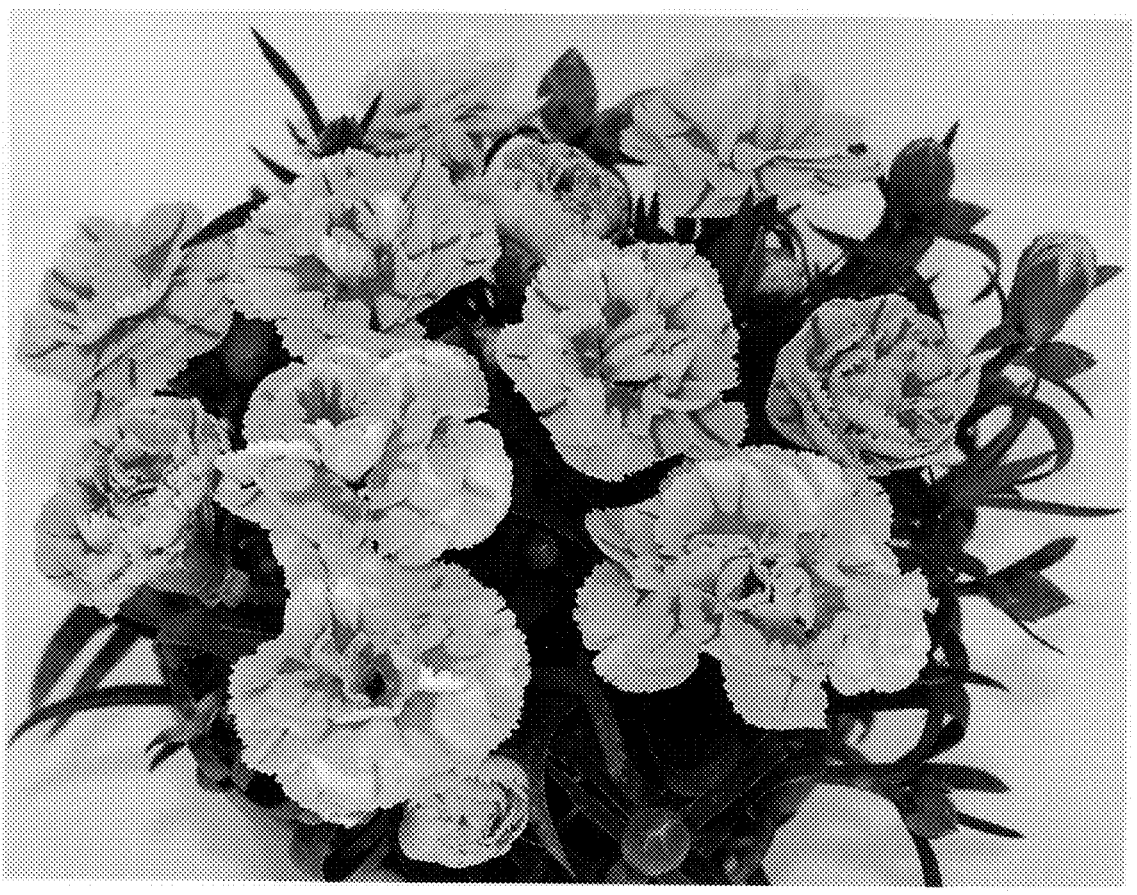

* * * * *